(12) United States Patent
Cocandeau et al.

(10) Patent No.: US 10,869,823 B2
(45) Date of Patent: Dec. 22, 2020

(54) COSMETIC COMPOSITION COMPRISING A PEPPERMINT EXTRACT

(71) Applicant: CHANEL PARFUMS BEAUTE, Neuilly sur Seine (FR)

(72) Inventors: Vincent Cocandeau, Saint Ouen (FR); Maeva Gillet, Paris (FR); Serge Holderith, Vincennes (FR); David Legangneux, Rambouillet (FR); Annie Lerisson, Montmagny (FR); Aurelien Rey, Paris (FR); Alix Toribio, Saint Ouen (FR); Lionel Weinberg, Perreux-sur-Marne (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 340 days.

(21) Appl. No.: 15/923,689

(22) Filed: Mar. 16, 2018

(65) Prior Publication Data

US 2018/0263877 A1    Sep. 20, 2018

(30) Foreign Application Priority Data

Mar. 16, 2017    (EP) .................................... 17305285

(51) Int. Cl.
*A61K 8/37*    (2006.01)
*A61Q 19/08*    (2006.01)
*A61K 8/9789*    (2017.01)
*A61K 8/34*    (2006.01)

(52) U.S. Cl.
CPC .............. *A61K 8/375* (2013.01); *A61K 8/347* (2013.01); *A61K 8/37* (2013.01); *A61K 8/9789* (2017.08); *A61Q 19/08* (2013.01)

(58) Field of Classification Search
None
See application file for complete search history.

(56) References Cited

FOREIGN PATENT DOCUMENTS

DE    10 2005 026 357 A1    12/2006

OTHER PUBLICATIONS

Najafian et al., "Polyphenolic contents and antioxidant activities of two medicinal plant species, Mentha piperita and Stevia rebaudiana, cultivated in Iran", Comparative Clinical Pathology, 2016, pp. 743-747, vol. 25, Issue 4, XP036000414.
Panya et al., "An Investigation of the Versatile Antioxidant Mechanisms of Action of Rosmarinate Alkyl Esters in Oil-in-Water Emulsions", Journal of Agriculture and Food Chemistry, 2012, pp. 2692-2700, XP 055226738.
EP Search Report, dated Jul. 4, 2017, from corresponding EP application No. 17 30 5285.

*Primary Examiner* — Aaron J Kosar
(74) *Attorney, Agent, or Firm* — Nixon & Vanderhye

(57) ABSTRACT

Cosmetic or dermatological composition including, in a physiologically acceptable medium, a hydrophilised extract of peppermint stems and use of such a composition as an antioxidant in a cosmetic or dermatological composition.

20 Claims, No Drawings

COSMETIC COMPOSITION COMPRISING A PEPPERMINT EXTRACT

FIELD OF THE INVENTION

The present invention relates to a cosmetic or dermatological composition comprising a peppermint extract coming from at least one species of mint (*Mentha piperita*). In particular, the present invention relates to a cosmetic composition capable of reducing the presence of free radicals involved in the phenomena of skin cell ageing. The invention also relates to the use of a peppermint extract as an antioxidant in a cosmetic or dermatological composition.

CONTEXT OF THE INVENTION

The production of free radicals is one of the major factors in the acceleration of skin ageing. It is known at the present time that 80% of external free radicals come from UV exposure, the remaining 20% come from pollution and climatic variations. It is therefore important to provide the skin with antioxidants, the only nutrients capable of trapping these reactive molecules that attach to the proteins, fatty acids and DNA of our cells.

Skin ageing, photo-ageing and the alterations that are associated with the presence of free radicals may manifest in various ways, including the following:
- loss of firmness and elasticity due to tissue loss at the epidermis and/or dermis;
- loss of radiance due to the reduction in microcirculation and a slowing down in cell renewal at the epidermis;
- the appearance of pigment spots associated with malfunctioning of the synthesis of melanin (or melanogenesis);
- skin dryness resulting from a reduction in the barrier function of the stratum corneum and slowing down of epidermal renewal.

There exists, because of this, a need to provide an antioxidant capable of reducing the presence of free radicals and thus to act on a set of causes of alterations in the skin due to ageing and/or to a modification of physiological mechanisms related to ageing caused by free radicals.

Extracts of natural origins are used more and more frequently in the dermocosmetic field. Peppermint is known for its antioxidant, calming, emollient, analgesic and anaesthetic properties. Rosmarinic acid, which comes from it, is known as one of the most antioxidant natural molecules in existence. It is also known that it is possible to modify the physicochemical properties of certain molecules chemically or biologically in order to modulate their effectiveness and to target their actions within the cells. Thus, according to the polarity, each of the molecules obtained will have a given action in the various cell compartments. For example, it is known that grafting a glycerol molecule makes it possible to have better bioavailability in aqueous media.

There therefore exists a requirement for a cosmetic or dermatological composition having antioxidant properties making it possible to effectively combat the presence of free radicals.

However, such a composition obtained from a plant extract and more particularly from peppermint requires an extract with high antioxidant properties.

It is to the merit of the applicant that it has revealed that, by proceeding with a quite specific extraction of peppermint, it was possible to boost its antioxidant properties compared with the extracts currently known.

SUMMARY OF THE INVENTION

The present invention was implemented with respect to the prior art described above, and the aim of the present invention is therefore to obtain a cosmetic or dermatological composition which, through its antioxidant capabilities, is capable of very greatly reducing the presence of free radicals involved in the phenomena of cell ageing of the skin as well as the use of such a composition for combating the presence of free radicals.

To solve the problem the present invention provides a peppermint extract (I) obtained by the extraction of peppermint stems with a mixture of hydroalcoholic solvents, preferably an ethanol/water mixture, and esterification with glycerol, said peppermint extract (I) comprising at least a compound of formula (I):

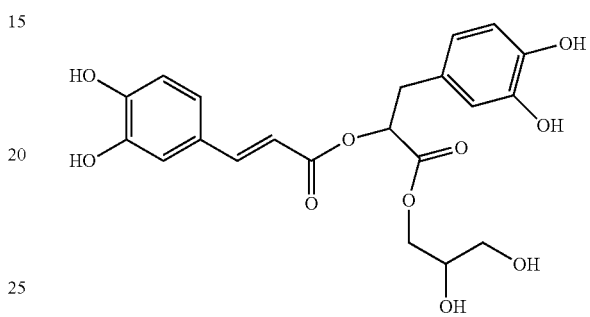

Thus the present inventors found that said extract (I) made it possible, through its antioxidant properties (demonstrated at example 4, table 3), to combat the presence of free radicals, which enabled them to end up with the present invention. The antioxidant properties of this extract make it possible to act on symptoms due to ageing, or to physiological mechanisms related to ageing, or to problems relating to these mechanisms at the epidermis and/or dermis. Cosmetic or dermatological composition in the present invention excludes medical applications.

The product of a hydroalcoholic extraction of dried stems of peppermint esterified with glycerol contains more compound of formula (I) compared with the extracts of the prior art, and has excellent antioxidant properties.

The extract (I) is preferentially obtained from at least one species of peppermint (*Mentha piperita*).

The genus *Mentha* belongs to the Lamiaceae family. This Lamiaceae family is an important family of plants comprising approximately 6000 species and around 210 genera, widely spread throughout the world and in all types of environments.

Mints are typical Lamiaceae (apart from the floral corolla, which is different from the bilabiate character) and belong to the *Mentha* genus. This genus comprises twenty-five species of evergreen or semi-evergreen aromatic hardy plants of Europe, Asia and Africa. The majority are cultivated for their aroma, for their flavour or their ornamental qualities. Their forms vary from creeping to bushy, and their flavour may be very strongly refreshing.

The species *Mentha×piperita* L. is a hybrid created in England, resulting from a cross between *Mentha spicata* and *Mentha aquatica*; its synonyms are *Mentha×adspersa* Moench, *Mentha×atrata* Ehrh., *Mentha×balsamea* Willd., *Mentha×concinna* Pérard, *Mentha×eriantha* K.Koch, *Mentha×odora* Salisb., *Mentha×piperoides* Malinv., *Mentha× reverchonii* Briq., *Mentha nigricans* Mill., *Mentha odorata* Sole.

It is also known by the common names: peppermint, mint, peppermin, menthe poivrée, Pfefferminze.

According to a second embodiment, the subject matter of the present invention is a cosmetic or dermatological composition characterised in that it comprises, in a physiologically acceptable medium, a mint extract (I) as defined previously.

Advantageously, the composition also comprises a hydroalcoholic extract of stems of peppermint (II) obtained by the extraction of stems with a mixture of hydroalcoholic solvents, preferably an ethanol/water mixture, comprising at least a compound of formula (II)

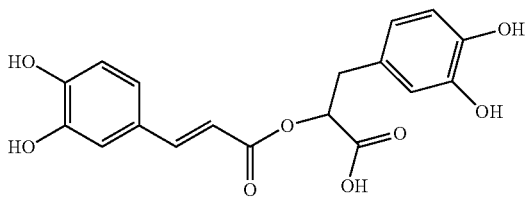 [SMILES: O=C(/C=C/c1ccc(O)c(O)c1)OC(Cc1ccc(O)c(O)c1)C(=O)O]

According to a particular embodiment, the composition according to the invention may in particular comprise a peppermint extract (I) and a peppermint extract (II) as defined previously, the ratio by weight of the extracts (I)/(II) preferably being between 0.5 and 2, and more preferentially 1.

According to a preferred embodiment, the composition also comprises a hydroalcoholic extract of stems of peppermint (II) previously described, and a peppermint extract (III) obtained by the extraction of peppermint stems with a mixture of hydroalcoholic solvents, preferably with an ethanol/water mixture, and esterification with octyl alcohol, said peppermint extract (III) comprising at least a compound of formula (III)

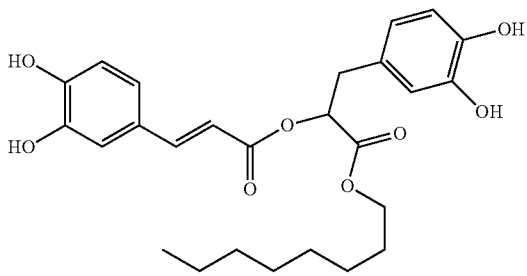 [SMILES: CCCCCCCCOC(=O)C(Cc1ccc(O)c(O)c1)OC(=O)/C=C/c1ccc(O)c(O)c1]

According to a preferred embodiment, the extracts (I), (II) and (III) are obtained solely from peppermint stems rather than from leaves or the complete plant.

The inventors found that a particular mixture of extracts (I) and (II), and more preferentially extracts (I), (II) and (III), had a particular synergy, which made it possible to obtain, unexpectedly, even greater antioxidant properties, as demonstrated by the results obtained at example 4.

In a preferred embodiment, the extract (II) is obtained by alcohol extraction by means of a monohydric alcohol and/or a glycol, optionally mixed with water.

Particularly advantageously, the composition comprises a mixture of extracts (I), (II) and (III), wherein the ratio by weight of extracts (II)/(III) is between 0.5 and 1.5 and the ratio by weight of extracts (I)/(II) is between 2 and 4.

Even more advantageously, the composition comprises a mixture of extracts (I), (II) and (III) wherein the ratio by weight of extracts (I)/(II)/(III) is 3/1/1.

The inventors observed, particularly unexpectedly, that these particular proportions had an increased antioxidant effect, as demonstrated by the results in table 3 of example 4. Moreover, according to the chosen polarity of the molecules present, said extracts will have a given action in the various cell compartments and will more easily cross the barriers formed by the various layers of the dermis and epidermis.

Advantageously, the composition is suited to topical application.

In a particular embodiment of the composition, said extract (I) or the mixture of extracts (I), (II) and optionally (III) represents a content ranging from 0.01 to 10% by weight, in particular from 0.1 to 10%, preferably from 1 to 5% by weight, with respect to the total weight of the composition.

The examples of cosmetic and dermatological compositions tested at example 5 demonstrated that these concentrations made it possible to preserve a remarkably high antioxidant activity once the active principle was introduced into a composition suited to topical application.

The cosmetic or dermatological composition according to the invention thus comprises an extract obtained according to a method for extracting peppermint stems comprising at least the steps such as:

1. taking peppermint stems, preferentially dried,
2. grinding said stems,
3. extracting said stems with a mixture of hydroalcoholic solvents preferably composed of an ethanol/water mixture at a temperature above 50° C.,
4. sieving in order to eliminate the plant residues,
5. preferentially decolouring by contact with activated charcoal for one hour, and then separating the mixture from the carbon residue by means of microfiltration in order to obtain an extract,
6. eliminating the alcoholic solvent, preferably by evaporation, and concentrating the extract,
7. acidifying with sulphuric acid in order to achieve a pH<3 and adding an organic solvent such as ethyl acetate,
8. separating the extract contained in the organic phase from the aqueous phase, eliminating the aqueous phase and then eliminating the organic solvent in order to obtain a powder, and
9. a functionalisation step by the addition of 1,3-propanediol, or glycerol, or octyl alcohol.

In a first variant of the invention, the composition comprises a peppermint extract (II) obtained according to a method for hydroalcoholic extraction of peppermint stems comprising the following steps:

1)—taking peppermint stems, preferentially dried,
2)—grinding said stems, typically to a fineness below 2 cm,
3)—preferentially extracting said stems twice with a mixture of hydroalcoholic solvents typically composed of 55% 96° ethanol and 45% water (v/v) under 60° C. conditions and for a minimum of 2 hours,
4)—sieving preferentially to 5 μm in order to eliminate the plant residues,
5)—preferentially decolouring by contact with activated charcoal for one hour in order to eliminate the pigments such as chlorophylls and xanthophylls and then separating the mixture from the carbon residue by means of microfiltration (to 1 μm) in order to obtain an extract,
6)—eliminating the alcoholic solvent, preferably by evaporation, and concentrating the extract, 7)—acidifying typically with sulphuric acid in order to achieve a pH<3 and adding an organic solvent, typically ethyl acetate, in order to effect liquid/liquid purification, 8)—separating the extract contained in the organic phase from the aqueous phase, eliminating the aqueous phase and then eliminating the organic solvent, for example under vacuum, in order to obtain a powder, 9)—preferentially adding 1,3-propanediol to said powder.

In a second variant of the invention, the composition comprises a peppermint extract (I) obtained according to a method comprising the following steps:

1)—taking the extract (II) previously obtained,

2)—adding glycerol to said powder,

3)—carrying out complete esterification of the rosmarinic acid and derivatives preferentially by adding an ion exchange resin to the previous mixture, for a minimum of 7 days at 70° C., and then eliminating the ion exchange resin by sieving, 4)—preferably decolouring by contact with activated charcoal for one hour and then eliminating the carbon residue by filtration (to 4 μm), 5)—adding glycerol and preferably an aqueous solution.

In a third variant of the invention, the composition comprises a peppermint extract (III) obtained according to a method comprising the following steps:

1)—taking the previously obtained extract (II),

2)—adding octyl alcohol to said powder,

3)—carrying out complete esterification of the rosmarinic acid by adding an ion exchange resin to the previous mixture for 7 days at 70° C., and then eliminating the ion exchange resin by sieving, 4)—preferably decolouring by contact with activated charcoal for one hour and then eliminating the carbon residue by filtration (to 4 μm), 5)—preferentially eliminating the residual octyl alcohol by evaporation and adding dipropylene glycol.

The inventors observed that the extracts obtained according to these various steps were particularly rich in compounds of interest and allowed a use thereof in cosmetic or dermatological compositions. The compounds of formulae (I), (II) and (III) previously mentioned are therefore preferentially obtained by these methods.

The invention also relates to the cosmetic use of a cosmetic or dermatological composition as defined above, comprising, in a physiologically acceptable medium, a peppermint extract (I) for an antioxidant effect, preferably by reducing the presence of free radicals involved in the phenomena of cell ageing of the skin.

Another subject matter of the invention is the use of a peppermint extract (I) as described above, as an antioxidant agent in a cosmetic or dermatological composition.

Advantageously, the composition according to the invention also comprises a compound chosen from an emollient or moistening agent, a gelling and/or thickening agent, a surfactant, an oil, an active agent, a dye, a preservative, an antioxidant, an active agent, an organic or inorganic powder, a sunscreen and a perfume.

Advantageously, said cosmetic or dermatological composition may be in the form of a powder, an emulsion, a microemulsion, a nanoemulsion, a suspension, a solution, a lotion, a cream, an aqueous or hydroalcoholic gel, a foam, a serum, a solution or an aerosol dispersion, or a lipid vesicle dispersion.

In the case of an emulsion, it may be a water-in-oil or oil-in-water emulsion.

The cosmetic or dermatological composition also comprises a solvent chosen according to the various ingredients and the form of administration.

By way of examples, mention can be made of water (preferably demineralised water), an alcohol such as ethanol, or a diethylene glycol ether such as ethoxydiglycol or diethylene glycol monomethyl ether.

Said cosmetic composition may also comprise an additive that is usual in the field, such as for example a compound chosen from an emollient or moistening agent, a gelling and/or thickening agent, a surfactant, an oil, an active agent, a dye, a preservative, an antioxidant, an active agent, an organic or inorganic powder, a sunscreen and a perfume.

In particular, said composition may contain:

One or more emollients that may be chosen for example from esters such as jojoba esters, fatty acid and fatty alcohol esters (octyldodecyl myristate, triethylhexanoin, dicaprylyl carbonate, isostearyl isostearate, caprylic/capric triglyceride), butters such as karite butters (butyrospernum parkii butter extract, shea butter ethyl esters, sold under the names Lipex Sheasoft, Lipex Shea-U, Lipex Shea, Lipex Shealight, Lipex Shea Tris) or moringa (moringa oil/hydrogenated moringa oil esters), waxes (*Acacia decurrens* flower wax & *Helianthus annuus* cera seed wax, C10-18 triglycerides), plant oils, phytosqualane, alkanes (undecane, tridecane).

Said emollient will be present in the composition in a proportion of around 0 to 30%, preferably 0.5 to 10% by total weight of the composition.

One or more moistening agents, such as polyols (glycerine, propylene glycol, propanediol), sugars, glycosaminoglycans such as hyaluronic acid and its salts and esters; and polyquaterniums such as Lipidure PMB.

Said moistening agent will be present in the composition in a proportion of around 0 to 30%, preferably 0.005 to 10% by total weight of the composition.

One or more gelling agents and/or thickeners of the aqueous phase, chosen for example from cellulose derivatives, gums of plant origin (guar, carob, alginates, carrageenans, pectins), of microbial origin (xanthan), clays (laponite), homo- and copolymers cross-linked or not, hydrophilic or amphiphilic, acryloylmethylpropane sulfonic acid (AMPS) and/or acrylamide and/or acrylic acid and/or salts or esters of acrylic acid (sold under the names Aristoflex AVC, Aristoflex AVS, Aristoflex HMB, Simulgel NS, Simulgel EG, Simulgel 600, Simulgel 800, Pemulen, Carbopol, Sepiplus 400, Seppimax zen, Sepiplus S, Cosmedia SP).

Said gelling and/or thickening agent will be present in the composition in a proportion of around 0 to 10% by total weight of the composition.

One or more surfactants, such as lecithins, sugar derivatives (derivatives of glucosides or xylosides sold under the name Montanov 68, Montanov 202, Montanov 82, Montanov L, Easynov), phosphates (C20-22 alkyl phosphate sold under the name Sensanov WR) present in a proportion of around 0 to 8%, preferably 0.5 to 3% by total weight of the composition.

One or more fats liquid at ambient temperature, commonly referred to as oils, volatile or non-volatile, hydrocarbon, silicone, linear, cyclic or branch, for example isododecane, cyclopentadimethylsiloxane, dimethicone, isononyl isononanoate, pentaerythrityl tetraisostearate, etc., preferably in a proportion of 0 to approximately 10%, preferably 0.5 to 5% by total weight of the composition.

One or more active agents of natural, biotechnological or synthetic origin having a biological activity and having efficacy on the skin via biological sites, for example chosen from vitamins such as vitamin C and derivatives thereof (ascorbyl glucoside, 3-o-ethyl ascorbic acid, ascorbyl tetraisopalmitate), vitamin A and derivatives thereof, vitamin E and derivatives thereof, vitamin B3 or niacinamide, oligoelements, allantoin, adenosine, peptides (palmitoyl tripeptide-1, palmitoyl tetrapeptide-7, palmitoyl pentapeptide-4, acetyl dipeptide-1 cetyl ester, acetyl tetrapeptide-5 sold under the names Matrixyl 3000, N-Palmitoyl-Rigin, Idealift, Eyeseryl), plant extracts (*Glycyrrhiza glabra* extract, *Centella asiatica* leaf extract, secale cereal seed extract), yeast extracts, alpha hydroxy acids, such as glycolic or lactic acid, beta hydroxy acids such as salicylic acid and derivatives thereof, etc.

Said active agent will be present in the composition in a proportion of around 0% to 10% by total weight of the composition.

One or more powders such as for example silica, nylon-12, cellulose, boron nitride, elastomer silicones (dimethicone/vinyl dimethicone crosspolymers and dimethicone crosspolymers sold under the name DC 9040, DC 9041, DC 9045, KSG-15, KSG-16, KSG-016F, KSG-18, lauryl dimethicone/vinyl dimethicone crosspolymers sold under the names KSG-31, KSG-32, KSG-41, KSG-42, KSG-43, KSG-44) preferably in a proportion from 0% to approximately 10% by total weight of the composition.

Other additives normally used in cosmetics may also be present in the composition according to the invention, in particular preservatives (phenoxyethanol, pentylene glycol, caprylyl glycol, chlorphenesin, etc.), antioxidants or perfumes well known in the technical field.

A person skilled in the art is able to choose, from all these possible additives, both the composition and the quantity thereof that will be added to the composition, so that the latter keeps all its properties.

The invention is illustrated non-limitatively by the following examples.

There are three different extracts referred to hereinafter; a peppermint extract (II), a peppermint extract (I) and a peppermint extract (III).

EXAMPLE 1

Preparation of a peppermint extract (II) from the hydroalcoholic extraction of dried stems and purification with ethyl acetate, in accordance with the following steps:

1) The dried peppermint stems are ground to a fineness below 2 cm,
2) The stems are next extracted twice with a mixture of solvents composed of 55% to 96° ethanol and 45% water (v/v) under conditions of 60° C. and a minimum of 2 hours,
3) The mixture is sieved (to 5 μm) in order to eliminate the plant residues,
4) The resulting mixture is subjected to decolouring by contact with activated charcoal for one hour in order to eliminate the pigments such as chlorophylls and xanthophylls,
5) The decoloured mixture is separated from the carbon residue by means of microfiltration (to 1 μm),
6) The ethanol of the mixture is eliminated by evaporation and the extract is concentrated,
7) The concentrated extract is acidified with sulphuric acid in order to achieve a pH of <3, and ethyl acetate is added in order to effect a liquid/liquid purification,
8) The higher ethyl acetate phase is separated from the lower aqueous phase. The ethyl acetate solvent of the higher phase is eliminated under vacuum in order to obtain a powder,
9) 1,3-propanediol is added to the powder. To facilitate solubilisation, ethanol may be added and eliminated by evaporation.

The resulting peppermint (II) is composed of 5% dry extract (w/w) and 95% 1,3-propanediol. This extract is mainly composed of rosmarinic acid in a proportion of between 1.5-2%.

EXAMPLE 2

Preparation of a hydrophilised mint extract (I) ( ) using hydroalcoholic extraction of dried stems, purified with ethyl acetate and esterified with glycerol, in accordance with the following steps:

1) Same steps as peppermint (II) from 1) to 8),
2) The powder is added to glycerine,
3) An ion exchange resin such as a cation exchange resin is added to the above mixture and complete esterification of the rosmarinic acid and derivatives thereof is carried out for 7 days minimum at 70° C. Next the ion exchange resin is eliminated by sieving,
4) The resulting mixture is subjected to decolouring by contact with activated charcoal for one hour. The carbon residue is next eliminated by filtration (to 4 μm),
5) Finally water and glycerol were added in order to obtain Hyros peppermint composed of 5% dry extract (w/w), 67% glycerol and 28% water.

This extract (I) is mainly composed of glyceryl rosmarinate in a proportion of 1-1.7%.

EXAMPLE 3

Preparation of a lyophilised mint extract (III) ( ) using hydroalcoholic extraction of dried stems, purified with ethyl acetate and esterified with octyl alcohol, in accordance with the following steps:

1) Same steps as peppermint (II) from 1) to 8),
2) The powder is added to octyl alcohol,
3) An ion exchange resin such as a cation exchange resin is added to the above mixture and complete esterification of the rosmarinic acid and derivatives thereof is carried out for 7 days minimum at 70° C. Next the ion exchange resin is eliminated by sieving,
4) The resulting mixture is subjected to decolouring by contact with activated charcoal for one hour. The carbon residue is next eliminated by filtration (to 4 μm),
5) The residual octyl alcohol is eliminated by evaporation and, finally, dipropylene glycol is added in order to obtain Liros peppermint composed of 5% dry extract (w/w) and 95% dipropylene glycol.

This extract (III) is mainly composed of octyl rosmarinate in a proportion of between 1.5 and 2.7%.

The raw material used consists for example of peppermint stems from a *Mentha piperita* species, which can be ground and reduced into the pieces in the usual way.

The *Mentha piperita* stems used for these extractions contain rosmarinic acid but also derivatives.

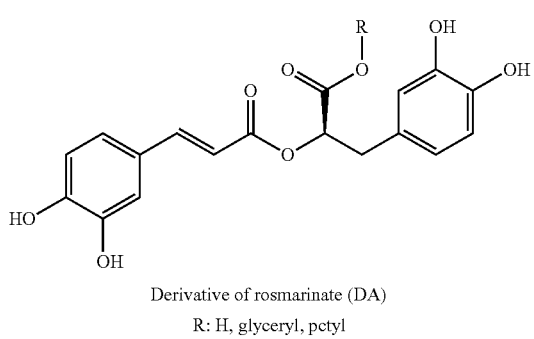

Derivative of rosmarinate (DA)

R: H, glyceryl, pctyl

EXAMPLE 4

Measurement of the Antioxidant Activity of the Extracts and Mixtures Thereof.

The total antioxidant activity is the ability of an antioxidant compound or of a set of antioxidant compounds to trap free radicals. It was assessed by means of the PAOT Technologie® developed by the Institut Européen des Antioxydants. This method gives the total antioxidant and oxidant activity (PAOT) of the matrix analysed.

The measurement is done in a liquid medium, by solubilisation of the product in a reaction medium, and then direct analysis of its activity in solution.

The reaction medium of the PAOT Technologie is composed mainly of physiological solutions with a pH of 6.7 to 7.2 (in order to simulate biological conditions). 20 µl of sample is mixed with 1 ml of reaction medium. Specific electrodes are immersed in the solution for a maximum of 7 minutes at a temperature between 24° and 27° C. The principle is based on the change in the ratio of the oxidised and reduced forms of the components of the medium.

This change results from the variation in the concentrations of the oxidised/reduced forms during the reaction (1) for the antioxidants and the reaction (2) for oxidants:

Reaction medium+$AO$ (antioxidant)=>reaction medium+$AOOx$ (result of oxidation of the antioxidant)  (1)

Reaction medium+$OA$ (oxidant)=>reaction medium+ $OA$ Red (result of the reduction of the oxidant)  (2).

The results can be expressed in PAOTScore® (total antioxidant activity) or POTScore® (total oxidising activity) units per litre or per gram of product analysed (PAOT Score/l or POT Score®/g of product). It can also be expressed in µM/l or µM/g of reference molecules (antioxidant and oxidant).

The experimental conditions are implemented in triplicate (n=3).

Definition of the extracts and mixtures thereof:
MEL 1: 100% peppermint (I)
MEL 2: 100% peppermint (II)
MEL 3: 100% peppermint (III)
MEL 4: 50% peppermint (I) and 50% peppermint (II)
MEL 5: 66.6% peppermint (I), 16.6% peppermint (II) and 16.6% peppermint (III)

The results are set out in the following table:

TABLE 1

|  | PAOT score |
| --- | --- |
| MEL 1 | 528 |
| MEL 2 | 481 |
| MEL 3 | 353 |
| MEL 4 | 559 |
| MEL 5 | 571 |

The total antioxidant activity is expressed as a reference equivalent. The equivalence is expressed in reference grams per litre of product. The higher the equivalence value, the greater the product efficacy.

In order to be considered to have very effective antioxidant properties, it is necessary for the PAOT-Score to be >50. Between 40 and 49 PAOT-Score the antioxidant activity is considered to be effective, and for a PAOT-S core of between 25 and 39 the antioxidant activity is assessed to be moderate.

All the samples derived from the extracts obtained in examples 1, 2 and 3 therefore show particularly remarkable antioxidant properties.

Control tests are carried out in order to measure the antioxidant activity of the solvents E15/177 ZEMA, E15/178 DPG (dilution 1/2) and E15/179 glycerol/water, their PAOT score remains below 3, which shows the absence of a role of antioxidant activity observed in the above samples.

It is found that the sample MEL1, the peppermint extract (I) has the best antioxidant activity score, and that the MEL4, the mixture of the 3 extracts in the ratio 3/1/1 has an unexpected synergy.

EXAMPLE 5

|  | F10 | F11 | F12 | F13 | F14 | F15 |
| --- | --- | --- | --- | --- | --- | --- |
| WATER | QSP | QSP | QSP | QSP | QSP | QSP |
| PHENOXYETHANOL | 0.5% | 0.5% | 0.5% | 0.5% | 0.5% | 0.5% |
| GLYCERIN | 3% | 3% | 3% | 3% | 3% | 3% |
| SODIUM PHYTATE & WATER & ALCOHOL | 0.05% | 0.05% | 0.05% | 0.05% | 0.05% | 0.05% |
| COPOLYMER OF SODIUM ACRYLATES AND LECITHIN (LECIGEL) | 2% | 2% | 2% | 2% | 2% | 2% |
| Active complex according to the invention* | 0 | 1% | 2% | 5% | 0 | 0 |
| Tocopherol acetate | 0 | 0 | 0 | 0 | 1% | 0 |
| Vitamin C | 0 | 0 | 0 | 0 | 0 | 1% |
| PAOT score | 47.83 | 87.17 | 82.67 | 129.33 | 43.92 | 44.03 |

*1% active complex according to the invention = 0.66% extract (I) + 0.17% extract (II) + 0.17% extract (III)

The PAOT score was also evaluated in a plurality of cosmetic compositions of the serum type at various concentrations. The compositions that gave the best results were obtained for those containing between 1% and 5% by weight active complex with respect to the total weight and more particularly for the composition comprising 5% by weight active complex, in the latter the antioxidant activity measured gave a PAOT score of approximately 130. This example of a cosmetic composition can therefore be considered to have very effective antioxidant properties.

It is also found that, at an equivalent concentration (1%), the formula with the active complex reveals a score twice as high with respect to the formula with the tocopherol and vitamin C references (their two scores being equivalents).

The invention claimed is:

1. A peppermint extract (I) obtained by the extraction of peppermint stems with a mixture of hydroalcoholic solvents and esterification with glycerol, said peppermint extract (I) comprising at least a compound of formula (I):

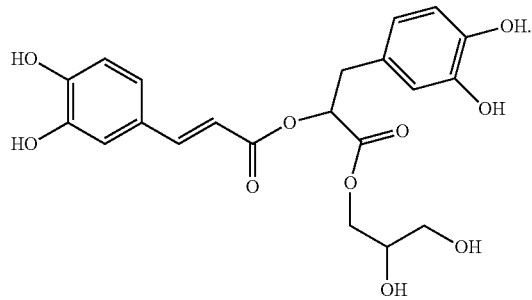 [SMILES: O=C(/C=C/c1ccc(O)c(O)c1)OC(Cc1ccc(O)c(O)c1)C(=O)OCC(O)CO]

2. A cosmetic or dermatological composition, comprising, in a physiologically acceptable medium, a peppermint extract (I) according to claim 1.

3. The composition according to claim 2, further comprising a peppermint extract (II) obtained by the extraction of stems with a mixture of hydroalcoholic solvents comprising at least a compound of formula (II):

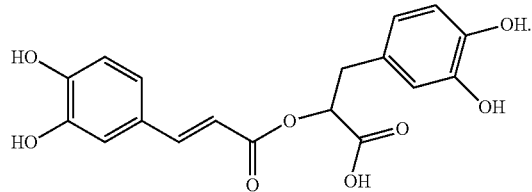 [SMILES: O=C(/C=C/c1ccc(O)c(O)c1)OC(Cc1ccc(O)c(O)c1)C(=O)O]

4. The composition according to claim 3, wherein the ratio by weight of the extracts (I)/(II) is between 0.5 and 2.

5. The composition according to claim 4, wherein the ratio by weight of the extracts (I)/(II) is 1.

6. The composition according to claim 3, wherein the hydroalcoholic extract (II) is obtained by alcohol extraction by means of a monohydric alcohol and/or a glycol.

7. The composition according to claim 3, further comprising a peppermint extract (III) obtained by the extraction of peppermint stems with a mixture of hydroalcoholic solvents, and esterification with octyl alcohol, said peppermint extract (III) comprising at least one compound of formula (III):

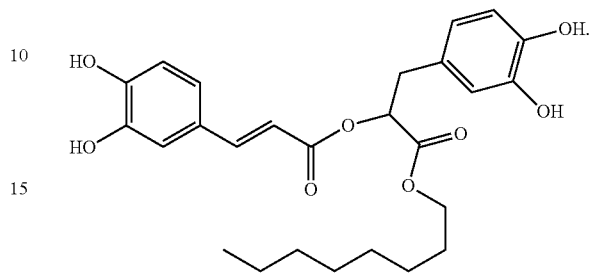

8. The composition according to claim 7, further comprising a mixture of extracts (I), (II) and (III), wherein the ratio by weight of the extracts (II)/(III) is between 0.5 and 1.5 and the ratio by weight of the extracts (I)/(II) is between 2 and 4.

9. The composition according to claim 7, characterised in that the ratio by weight of the extracts (I)/(II)/(III) is 3/1/1.

10. The composition of claim 7, wherein the mixture of hydroalcoholic solvents is an ethanol/water mixture.

11. The composition of claim 3, wherein the mixture of hydroalcoholic solvents is an ethanol/water mixture.

12. The composition according to claim 3, wherein the hydroalcoholic extract (II) is obtained by alcohol extraction by means of a monohydric alcohol and/or a glycol mixed with water.

13. The composition according to claim 1, wherein the composition is suited to topical application.

14. The composition according to claim 1, wherein said extract (I) or the mixture of extracts (I) and (II) represents a content ranging from 0.01% to 10% by weight, with respect to the total weight of the composition.

15. The composition of claim 14, wherein the content ranges from 0.1% to 10% by weight.

16. The composition of claim 14, wherein the content ranges from 1% to 5% by weight.

17. A cosmetic or dermatological composition comprising the peppermint extract (I) according to claim 1.

18. The peppermint extract of claim 1, wherein the mixture of hydroalcoholic solvents is an ethanol/water mixture.

19. The composition according to claim 1, wherein said extract (I) or the mixture of extracts (I), (II), and (III) represents a content ranging from 0.01% to 10% by weight, in particular from 0.1% to 10% with respect to the total weight of the composition.

20. A method for producing an antioxidant effect by reducing a presence of free radicals involved in the phenomena of cell ageing of the skin, comprising applying an effective amount of a composition according to claim 1.

* * * * *